United States Patent [19]

Buckle et al.

[11] 4,454,136

[45] Jun. 12, 1984

[54] SUBSTITUTED BENZOPYRANOTRIAZOLES AND ANTIALLERGIC USE

[75] Inventors: Derek R. Buckle, Redhill; Harry Smith, Maplehurst, Nr Horsham, both of England

[73] Assignee: Beecham Group Limited, England

[21] Appl. No.: 302,460

[22] Filed: Sep. 15, 1981

Related U.S. Application Data

[63] Continuation of Ser. No. 224,966, Jan. 14, 1981, abandoned.

[30] Foreign Application Priority Data

Jan. 19, 1980 [GB] United Kingdom ............... 8001855

[51] Int. Cl.³ .................. A61K 31/41; C07D 491/052
[52] U.S. Cl. .................... 424/245; 424/240; 548/101; 548/255; 548/256; 568/644
[58] Field of Search ............... 548/101, 256; 424/245, 424/269

[56] References Cited

U.S. PATENT DOCUMENTS 3,968,119 7/1976 Harnisch ............................ 548/256
4,248,879 2/1981 Buckle et al. ....................... 424/269

FOREIGN PATENT DOCUMENTS 7727 2/1980 European Pat. Off. ............ 424/269
1433270 4/1976 United Kingdom ............... 424/273

OTHER PUBLICATIONS

Harrison, Chem. Commun., 1969, p. 616.
Feutrill et al., Tetrahedron Letters No. 16, pp. 1327–1328 (1970).
Williard et al., Tetrahedron Letters, vol. 21, pp. 3731–3734 (1980).

Primary Examiner—Alton D. Rollins
Attorney, Agent, or Firm—Jacobs & Jacobs

[57] ABSTRACT

Compounds of the formula (I):

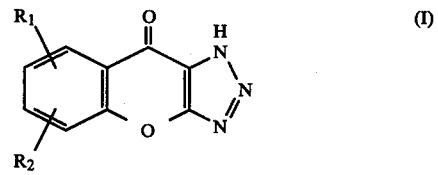

and pharmaceutically acceptable salts thereof, wherein $R_1$ is hydrogen or $C_{1-6}$ alkyl, and $R_2$ is hydroxy, $C_{1-4}$ alkylsulphonyloxy or p-toluenesulphonyloxy are useful for the prophylaxis and treatment of diseases due to allergic response in mammals. Processes for their preparation are described.

45 Claims, No Drawings

SUBSTITUTED BENZOPYRANOTRIAZOLES AND ANTIALLERGIC USE

CROSS-REFERENCE

This is a continuation of Ser. No. 224,966 filed Jan. 14, 1981, now abandoned.

This invention relates to a series of substituted benzopyranotriazoles, to a method for their preparation and their use as anti-allergic agents.

It is generally recognised that certain cells, e.g. mast cells are activated by antibody-antigen combinations and release substances which mediate an allergic response. We have discovered a novel class of 9-oxo-1H,9H-benzopyrano[2,3-d]-v-triazole derivatives which inhibit this type of antigen-induced response in mammals, and are therefore of value in the prophylaxis of diseases in which the symptoms are controlled by mediators of the allergic response. Examples of such diseases include bronchial asthma, rhinitis, hayfever and allergic eczema.

Accordingly, the present invention provides a compound of the formula (I):

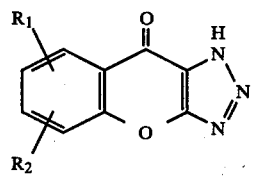

and pharmaceutically acceptable salts thereof, wherein $R_1$ is hydrogen or $C_{1-6}$ alkyl, and $R_2$ is hydroxy, $C_{1-4}$ alkylsulphonyloxy or p-toluenesulphonyloxy.

Suitable examples of $R_1$ include hydrogen, methyl, ethyl and n and iso-propyl. More suitably $R_1$ is hydrogen methyl, or n-propyl.

Suitably $R_2$ is hydroxy. Also, $R_2$ may suitably be methanesulphonyloxy or p-toluenesulphonyloxy. It is believed that when $R_2$ is a sulphonyl, then it is most suitably methanesulphonyl.

Most suitably $R_1$ (when other than hydrogen) is in the 5-position (that is, substituting the carbon atom adjacent the oxygen atom joined bridgehead carbon atom).

Most suitably $R_2$ is in the 6-position (that is, substituting the carbon atom meta- to the oxygen atom joined bridgehead carbon atom).

The triazole moiety of the compounds of formula (I) has an acidic hydrogen, and accordingly may form salts. Examples of pharmaceutically acceptable salts falling within the scope of this invention include the aluminium, alkali metal and alkaline earth metal salts such as the sodium, potassium and magnesium salts; and salts with ammonia, organic bases and amino compounds.

From the aforesaid it will be appreciated that one group of compounds of the formula (I) is of formula (II):

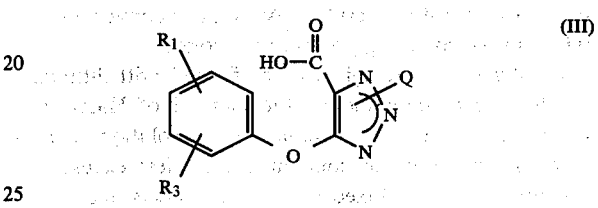

wherein $R_1$ and $R_2$ are as defined in formula (I).

Suitable and preferred $R_1$ and $R_2$ are as so described under formula (I).

The invention also provides a process (a) for the preparation of a compound of the formula (I), which process comprises the cyclisation of a compound of the formula (III)

wherein Q is hydrogen or an N-protecting group, $R_1$ is hydrogen or $C_{1-6}$ alkyl, $R_3$ is $C_{1-4}$ alkylsulphonyloxy or p-toluenesulphonyloxy, and thereafter if necessary hydrolysing the thus formed compound of the formula (I) wherein $R_2$ is $C_{1-4}$ alkylsulphonyloxy or p-toluenesulphonyloxy to the corresponding compound wherein $R_2$ is hydroxy; and converting Q when an N-protecting group to hydrogen.

The cyclisation is suitably carried out in the presence of polyphosphoric acid or phosphorus pentoxide and methanesulphonic acid.

The temperature for the cyclisation is suitably elevated, i.e. above 40° C. but less than 120° C. We have found temperatures between 80° and 105° C. to be convenient.

When the phenyl group of the compound of formula (III) is non-symmetric about the ring-O bond and the 2- and 6-positions with respect to the triazolyloxy side chain taken as 1 are unsubstituted then a mixture of two isomers results from cyclisation. These may be separated conventionally for example by fractional crystallisation or column chromatography.

Q may suitably be an N-protecting group removable by acidolysis with a strong acid. Suitable examples of Q include labile benzyl groups or trityl. Examples of labile benzyl groups include benzyl substituted in the phenyl ring by one or more $C_{1-4}$ alkoxy groups, such as 4-methoxy, 2,4-dimethoxy or 2,4,6-trimethoxy-benzyl. A particularly suitable example of Q is 4-methoxy-benzyl.

Q may be removed in any convenient way which does not disrupt any other part of the molecule, such as by acidolysis. Strong acids such as trifluoroacetic or methanesulphonic acids are suitable. The reaction may of course be monitored by n.m.r. spectroscopy or high pressure liquid chromatography but we have found that a temperature of 50° to 70° C. and a reaction time of 2 to 9 hours are appropriate.

If necessary, the subsequent hydrolysis may be carried out under conventional alkaline conditions.

The reaction also provides a second, preferred process (b) for the preparation of the compounds of the formula (I) which process comprises the dealkylation of a compound of the formula (IV):

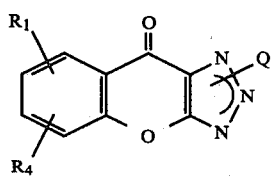

wherein Q is hydrogen or an N-protecting group, $R_4$ is $C_{1-4}$ alkoxy and $R_1$ is hydrogen or $C_{1-6}$ alkyl; and thereafter if necessary sulphonylating the thus formed compound of the formula (I) wherein $R_2$ is hydroxy to the corresponding compound wherein $R_2$ is $C_{1-4}$ alkylsulphonyloxy or p-toluenesulphonyloxy, and converting Q when an N-protecting group to hydrogen.

Dealkylation may suitably be effected with lithium iodide in 2,4,6-collidine by the method of Harrison, Chem. Commum, 1969, 616, in which a solution of the ether in dry collidine containing a modest excess of lithium iodide is refluxed for up to 24 hours under an inert atmosphere such as nitrogen.

It may also suitably be effected with boron-trihalidedimethylsulphide complexes by the method of Williard et al., Tetrahedron Letters, 1980, 3731, in which a two to four-fold excess of the complex in 1,2-dichloroethane is refluxed with the ether for up to 30 hours under an inert atmosphere such as nitrogen.

Suitable reaction conditions for the conversion of Q are as described for process (a).

Demethylation may suitably be effected with a base such as sodium thioethoxide in a polar solvent such as dimethylformamide, at moderately elevated temperatures such as 130° to 170° C., following the procedure of Feutrill et al., Tet. Letters, 1970, 1327. Reflux for 24 hr. in dimethylformamide is usually sufficient for reaction.

It will thus be seen that the invention provides a third process (a) for the preparation of compounds of the formula (I) which process comprises the conversion to hydrogen of a group $Q^1$ in a compound of the formula (V):

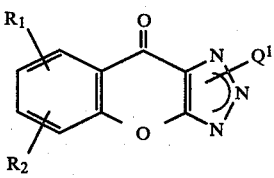

wherein $Q^1$ is an N-protecting group as defined and the remaining variables are as defined in formula (I).

Suitable reaction conditions for the conversion of $Q^1$ to hydrogen are described under process (a).

Compounds of the formula (V) of course may be prepared by process (a) or (b) from the corresponding compound of formula (III) or (IV) respectively.

Compounds of the formula (IV) may be prepared by the cyclisation of a compound of the formula (VI):

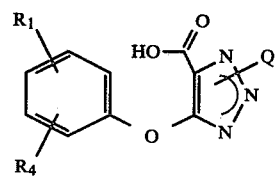

wherein Q, $R_1$ and $R_4$ are as defined in formula (IV).

The cyclisation is suitably effected under the same conditions as that of the compound of the formula (III).

Alternatively, when Q is an N-protecting group, the compound of the formula (VI) may be converted to its acid chloride (for example by treatment with thionyl chloride under conditions conventional for such reactions), and cyclisation of the acid chloride effected under Friedel-Crafts conditions, eg in dichloromethane, optionally under reflux, in the presence of aluminium trichloride.

Intermediates of the formulae (III) and (VI) may be represented by a common formula (VII):

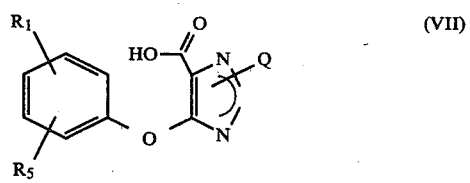

wherein $R_5$ is $R_3$ or $R_4$ as defined in formulae (III) and (IV).

Compounds of the formula (VII) wherein $R_4$ is $R_3$, ie of formula (III) may be prepared by sulphonylation of the corresponding compound of formula (VIII):

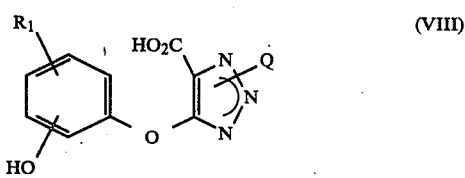

This sulphonation is carried out in conventional manner.

It should be noted that when mesylation is desired, this may suitably be carried out with a solution of phosphoric oxide in anhydrous methanesulphonic acid, and if the reaction temperature is held at about 95° C. this mesylate gradually cyclises to the corresponding compound of formula (I) as defined above.

The compound of formula (III) may alternatively be prepared by sulphonylation of an ester of formula (IX):

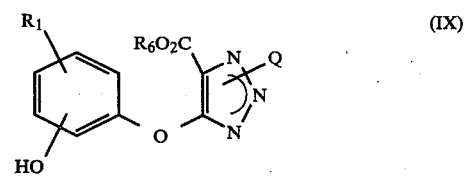

wherein $R_6$ is $C_{1-6}$ alkyl, such as ethyl and subsequent de-esterification.

An analogous conventional etherification process may also be used for compounds of the formula (VI), but Q must then be an N-protecting group in the compound of formula (IX) which may be converted subsequently to hydrogen, if desired.

The compound of formula (IX) is suitably prepared by hydrogenation of a compound of formula (X):

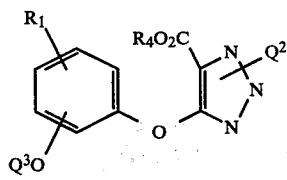 (X)

wherein $Q^2$ is a hydrogenolysable N-protecting group; and $Q^3$ is a hydrogenolysable O-protecting group to give a compound of formula (IX) as defined above, and subsequent de-esterification (with for example sodium hydroxide).

Suitable groups $Q^2$ and $Q^3$ include benzyl, 4-methylbenzyl and 4-nitrobenzyl and $Q^1$ as hereinbefore defined.

The aforesaid hydrogenation is conveniently carried out under conditions which remove both the protecting groups, for example with a palladium catalyst at about 1000 psi and 70°–100° C. However a stepwise hydrogenation is possible, as the O-protecting group can be removed selectively under mild conditions and by suitable choice, readily appovent to the skilled man, of the O- and N-protecting groups.

The compounds of formula (X) may themselves be prepared by reacting a monobenzylated dihydroxybenzene of formula (XI):

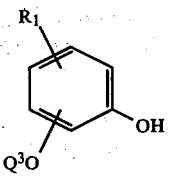 (XI)

as its sodium salt, with a chloro ester of formula (XII):

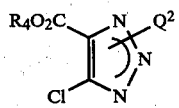 (XII)

Although compounds of the formula (XII) wherein $R_5$ is $C_{1-4}$ alkoxy $R_4$ may be prepared via compounds of the formulae (IX) and (X), it is preferred to prepare them directly by reaction of a compound of the formula (XII) with a compound of the formula (XIII):

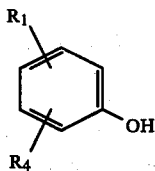 (XIII)

wherein the variables are as hereinbefore defined.

The salts of the compounds of the formula (I) may be prepared in the usual manner from the corresponding "free" compounds of the formula (I).

It is believed that the intermediates described above are all novel with the exception of compounds of formula (XIII) and as such form an important aspect of the present invention.

In order to use the compounds of the invention as medicinal agents, they will be formulated into pharmaceutical compositions in accordance with standard pharmaceutical procedure.

The invention also includes a pharmaceutical composition comprising a compound of formula (I) or a pharmaceutically acceptable salt thereof and a pharmaceutically acceptable carrier, for the prophylaxis or treatment of diseases due to an allergic response in mammals, especially human beings.

Compounds of formula (I) may be administered topically or systemically.

Topical formulations for administration to the skin include lotions and creams. Topical formulations for administration to the respiratory tract include solutions for application via a nebulizer or as an aerosol, or as a snuff or a microfine insufflatable powder. The active ingredient in an insufflatable powder has a small particle size i.e. less than 50 microns and preferably less than 10 microns. The active material is co-presented with a solid carrier such as lactose which has a particle size of less than 50 microns.

Systemic administration may be achieved by rectal, oral or parenteral administration. A typical suppository formulation comprises the active compound with a binding agent and/or lubricating agent such as gelatin or cocoa butter or other low melting vegetable waxes or fats. Typical parenteral compositions comprise a solution or suspension of the active material in a sterile aqueous carrier of parenterally acceptable oil.

Compounds of formula (I) which are active when given orally may be compounded in the form of syrups, tablets, capsules and lozenges. A syrup formulation will generally consist of a suspension or solution of the compound in a suitable liquid carrier such as ethyl alcohol, glycerine or water with a flavouring or colouring agent. Where the composition is in the form of a capsule, the solid in granular form optionally with a binding agent is encased in a gelatin shell. Where the composition is in the form of a tablet, any suitable pharmaceutical carrier routinely used for preparing solid formulations may be used. Examples of such carriers include magnesium stearate, starch, lactose, glucose, sucrose, rice flour and chalk. Preferably the composition is in unit dose form such as a pill, capsule or metered aerosol so that the patient may administer to himself a single dose.

Where appropriate, small amounts of anti-asthmatics and bronchodilators for example sympathomimetic amines such as isoprenaline, isoetharine, salbutamol, phenylephrine and ephedrine; xanthine derivatives such as theophylline and aminophylline; and corticosteroids such as prednisolone and adrenal stimulants such as ACTH may be included. As in common practice, the compositions will usually be accompanied by written or printed directions for use in the medical treatment concerned, in this case as an anti-allergic agent for treatment of, for example, asthma, hayfever or rhinitis.

In any of the foregoing formulations, a suitable dosage unit might contain from 1 to 500 mg of active ingredient. The effective dose of compound of formula (I) depends on the particular compound employed, the condition of the patient and on the frequency and route of administration, but in general is in the range of from 0.01 mg/kg/day to 50 mg/kg/day of the patient's body weight.

The following Examples illustrate the preparation and properties of some compounds within the scope of this invention.

EXAMPLE 1

(a) 3-Benzyloxy-2-methylphenol

Anhydrous potassium carbonate (30.4 g.) was added to a stirred solution of 2-methylresorcinol (24.8 g) in N,N-dimethylformamide (DMF, 250 ml) and benzyl chloride (25.3 g) was added over 15 minutes. The mixture was heated to 80° C. and maintained at this temperature overnight with continued stirring. On cooling the DMF was removed in vacuo to give an oil which was partitioned between water and ether. The dried ethereal phase was evaporated and chromatographed on silica eluting with chloroform to give 9.78 g (23%) of the title compound of mp 58°–59° C. (Found; C, 78.16; H, 6.63; $C_{14}H_{14}O_2$ requires C, 78.48, H, 6.58%).

(b) Ethyl 1-benzyl-5-(3-benzyloxy-2-methylphenoxy)-v-triazole-4-carboxylate

A 50% dispersion of sodium hydride (1.68 g, 0.035 mole) was added to a stirred solution of 3-benzyloxy-2-methylphenol (7.5 g, 0.035 mole) in dry DMF (200 ml) and to the resulting sodium salt was added a solution of ethyl 1-benzyl-5-chloro-v-triazole-4-carboxylate (9.30 g; 0.035 mole) in dry DMF (20 ml). The reaction mixture was heated with stirring at 80° C. for 24 hours and then cooled. Removal of the DMF in vacuo gave a dark oil which was taken up in chloroform, washed with water and dried. Evaporation gave an oil which crystallized on standing. Recrystallization gave 10.27 g (66%) of product of mp 98°–99° C. (Found; C, 70.48; H, 5.76, N, 9.54; $C_{26}H_{25}N_3O_4$ requires C, 70.41; H, 5.68, N, 9.48%)

(c) Ethyl 5-(3-hydroxy-2-methylphenoxy)-1H-v-triazole-4-carboxylate

Hydrogenolysis of a solution of ethyl 1-benzyl-5-(3-benzyloxy-2-methylphenoxy)-v-triazole-4-carboxylate (10 g) in ethanol (300 ml) over 10% palladium on charcoal at 100° C. and 1000 psi resulted in a clean removal of both the O- and N-benzyl groups within 3 hours. On cooling and removal of the catalyst by filtration evaporation of the solvent gave an oil which after filtration through a kieselgel column in chloroform gave 4.20 g (71%) of product of mp 120°–122° C. (Found; C, 54.62, H, 5.04; N, 16.19; $C_{12}H_{13}N_3O_4$ requires C, 54.75; H, 4.98; N, 15.96%).

(d) 5-(3-Hydroxy-2-methylphenoxy)-1H-v-triazole-4-carboxylic acid

Hydrolysis of ethyl 5-(3-hydroxy-2-methylphenoxy)-1H-v-triazole-4-carboxylate (2 g) with 5% aqueous sodium hydroxide (30 ml) at 80° C. over 1 hour afforded the acid which was isolated by acidification of the cooled (0° C.) solution. Recrystallization from aqueous ethanol gave 1.47 g (82%) of material of mp 141°–143° C. (Found; C, 50.71; H, 3.85, N, 17.70; $C_{10}H_9N_3O_4$ requires: C, 51.06; H, 3.86; N, 17.87%).

(e) 6-Mesyloxy-5-methyl-9-oxo-1H,9H-benzopyrano[2,3-d]-v-triazole

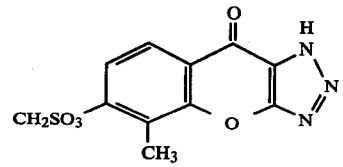

(i) To a solution of phosphoric oxide (21 g) in 98% methane sulphonic acid (90 g) at 60° C. was added 5-(3-hydroxy-2-methylphenoxy)-1H-v-triazole-4-carboxylic acid (2.8 g) with stirring and the mixture maintained at 100° C. After 22 hours at this temperature hplc monitoring showed the absence of starting material. The mixture was cooled, diluted with ice water and the product extracted into ethyl acetate. Evaporation of the dried extracts gave an oily solid which was recrystallized from ethanol in the presence of charcoal to give 1.39 g (40%) of the title compound of mp 183°–190° C. Further recrystallization gave material of mp 211°–212° C., δ(DMSO) 2.50 (3H, s); 3.58 (3H, s); 4.6 (broad exchangeable), 7.88 (2H, AB quartet J 9.0 Hz; Δν57 Hz), M+ 295.0265 ($C_{11}H_9N_3SO_5$) (Found: C, 44.65; H, 2.65 N, 13.75; $C_{11}H_9N_3SO_5$ requires C, 44.4; H, 3.05; N, 14.2%)

(ii) A similar treatment of 5-(3-mesyloxy-2-methylphenoxy) 1H-v-triazole-4-carboxylic acid (0.1 g, mp 144° C., prepared from the hydroxy compound and $P_2O_5$ in methane sulphonic acid at 70° C.) gave, after recrystallization from ethanol, 0.07 g (74%) of cyclic product of mp 205°–207° C. and identical with that prepared above.

(f) 6-Hydroxy-5-methyl-9-oxo-1H,9H-benzopyrano[2,3-d]-v-triazole

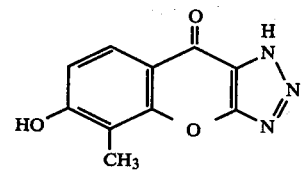

A mixture of 6-mesyloxy-5-methyl-9-oxo-1H,9H-benzopyrano[2,3-d]-v-triazole (0.1 g) and 1.25 M aqueous sodium hydroxide was stirred at 80° C. for 2 hours, cooled and cautiously acidified to pH 1. The white solid which separated was filtered off, washed well with water and dried to give 0.057 g (77.5%) of free hydroxy compound. Recrystallization from ethyl acetate-petrol gave material of m.p. 291°–292° C. (dec), $ν_{max}$ (mull) 3170, 2600 (broad), 1645, 1610, 1560, 1545 cm$^{-1}$, δ (DMSO) 2.29 (3H, s), 6.97 (1H, d, J 9 Hz), 7.90 (1H, d, J 9 Hz), 11 ppm 1H exchangeable proton. (Found, C, 55.31; H, 3.03; N, 18.78 ($C_{10}H_7N_3O_3$ requires, C, 55.30; H, 3.25; N, 19.35%). M+ 217.0489 ($C_{10}H_7N_3O_3$).

EXAMPLE 2

(a) Ethyl 1-benzyl-5-(3-methoxyphenoxy)-v-triazole-4-carboxylate

A 50% dispersion of sodium hydride in mineral oil (6.40 g, 0.13 mole), was added to a stirred solution of 3-methoxyphenol, (16.40 g, 0.13 mole), in dry DMF, (500 ml), and to the resulting sodium salt was added ethyl 1-benzyl-5-chloro-v-triazole-4-carboxylate, (35.0 g, 0.13 mole). The reaction mixture was heated with stirring at 70° C. for 21 hours and cooled.

Removal of the DMF in vacuo gave a brown oil which was taken up in ether, washed with 1M sodium hydroxide solution, water and brine and dried (MgSO$_4$). Evaporation gave a red oil which crystallized on trituration with ether/petrol ether 40°–60° C. [1:1].

Recrystallization from ether/petrol ether 60°–80° C. gave 33.75 g (53%) of product of mp 52°–53° C. (Found; C, 64.51; H, 5.27; N, 12.05; $C_{19}H_{19}N_3O_4$ requires C, 64.58; H, 5.42; N, 11.89%).

(b) Ethyl 5-(3-methoxyphenoxy)-1H-v-triazole-4-carboxylate

Hydrogenolysis of a solution of ethyl 1-benzyl 5-(3-methoxyphenoxy)-v-triazole-4-carboxylate, (17.27 g) in ethanol, (300 ml), over 10% palladium on charcoal at 100° C. and 1000 psi resulted in clean removal of the N-benzyl group in 2.5 hours. On cooling and removal of the catalyst by filtration, evaporation of the solvent gave an orange oil which crystallized on trituration.

Recrystallization from ethanol/water gave 9.16 g, (71%) of product of mp 104°–5° C. (Found C, 54.92; H, 4.88; N, 15.71, $C_{12}H_{13}N_3O_4$ requires C, 54.75; H, 4.98; N, 15.96%).

(c) 5-(3-Methoxyphenoxy)-1H-v-triazole-4-carboxylic acid

Hydrolysis of ethyl 5-(3-methoxyphenoxy)-1H-v-triazole-4-carboxylate, (9.10 g), with 5% aqueous sodium hydroxide (110 ml), at 80° C. for 1 hour afforded the acid which was isolated after acidification of the cooled, (0° C.), solution. Recrystallization from ethyl acetate/petrol ether 40°–60° C. gave 6.20 g (76%), of material of mp 133°–4° C., (dec), (Found; C, 51.31; H, 3.60; N, 17.88. $C_{10}H_9N_3O_4$ required C, 51.07; H, 3.86; N, 17.80%).

(d) 6-Methoxy-9-oxo-1H,9H-benzopyrano [2,3-d]-v-triazole and 8-methoxy-9-oxo-1H,9H-benzopyrano [2,3-d]-v-triazole

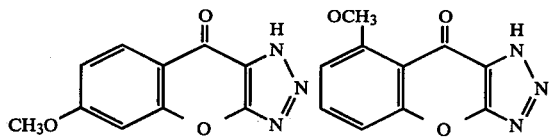

To a solution of phosphorus pentoxide (40 g) in 98% methanesulphonic acid, (100 g), at 80° C. was added 5-(3-methoxyphenoxy)-1H,-v-triazole-4-carboxylic acid, (5.50 g), with vigorous stirring and the brown solution maintained at 80° C. After 4 hours hplc monitoring showed the absence of starting material. The solution was cooled, diluted with ice water and left to stand overnight. The pink precipitate was collected by filtration to yield 4.1 g, (75%), of the 6-methoxy and 8-methoxy mixed isomers in the ratio 2:1 respectively. The pure isomers could be separated by fractional crystallization from ethanol.

Data of pure 6-methoxy isomer mp 270°–1° C. (dec), δ, DMSO-d6; 3.94, (3H,s,), 7.09, (1H,dd,J 2 & 7 Hz) 7.27 (1H, d,J 2 Hz), 8.12(1H,d,J 7 Hz). (found; C, 54.97; H, 3.54; N, 19.51; $C_{10}H_7N_3O_3$ requires C, 55.30; H, 3.25; N, 19.35%).

Data of pure 8-methoxy isomer mp 258°–60° C., δ, DMSO-d6; 3.92, (3H,s), 7.06 (1H, dd, J 8 Hz), 7.24 (1H, dd, J 8 Hz), 7.77 (1H, t, J 8 Hz) (Found; C, 55.31; H, 3.29; N, 19.64; $C_{10}H_7N_3O_3$ requires C, 55.30; H, 3.25; N, 19.35%).

(e) 6-Hydroxy-9-oxo-1H,9H-benzopyrano[2,3-d]-v-triazole

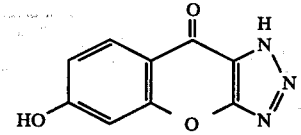

A 50% dispersion of sodium hydride (4.30 g, 0.09 m), was added to a stirred solution of ethanethiol (5.64 g, 0.09 m), in dry DMF, (90 ml), and to the resulting sodium salt was added 6-methoxy-9-oxo-1H,9H-benzopyrano [2,3-d]-v-triazole (2.25 g, 0.01 m). The mixture was heated, with stirring to 120° C. for 1.5 hours when TLC showed no starting material. The reaction was cooled and poured into ice water. The product was isolated by acidification of the solution. Recrystallization from aqueous DMF gave 1.80 g, (85%), of material mp 300° C. (dec), δ, DMSOd6; 6.94(2H,m), 8.08 (1H,d,J 9 Hz) 11.01 (1H,s, exchanges with D$_2$O).

I.r. $\nu$ max (mull)cm$^{-1}$ 3215, 1650, 1580, 1550

M.s. M+ 203.0337 ($C_9H_5N_3O_3$)

Pharmacology

Passive Cutaneous Anaphylaxis (PCA)

Serum containing heat-labile homocytotropic antibody was raised in rats to crystallized ovalbumin XOA by the method of Mota (I. Mota, Immunology, 7, 681, (1964)) using Bordettela pertussis vaccine as adjuvant.

Passive cutaneous anaphylaxis (PCA) was carried out by a method based on that of Ovary and Bier, (A. Ovary and O. G. Bier, Proc. Soc. Exp. Bio. Med 81, 584, (1952)) as modified by Goose and Blair. (Immunology 16, 749 (1969)).

Male Wistar rats of 250–300 g were give 0.1 ml of each of six twofold serial dilutions of pooled antiserum in 0.9% saline injected intradermally into separate sites on their shaved backs. Later (72 hours) the animals were challenged by intravenous injection of 0.3 ml of a 1% solution of ovalbumin in an isotonic solution of saline buffered with 0.05 M, pH 7.2, Sorenson Buffer (PBS), mixed with 0.2 ml of a 5% solution of Pontamine Sky Blue (6BX C.I. 24410, Raymond A. Lamb, London) in isotonic saline. The rats were killed after 20 minutes and the diameter of the blue wheals at the antibody injection sites were measured on the outer surface of the skin. The starting dilution of the serum was adjusted so that there was no response, after challenge, at the injection site of the highest dilution and a maximum response at the lowest dilutions. Typically six twofold serial dilutions of the serum from ¼ to 1/128 were used.

Compounds were tested for their ability to reduce the diameter of the wheals at those intradermal sites which in control animals gave less than maximum response. Each dose of the compound was administered to six rats at a measured time prior to intravenous challenge with ovalbumin. Control groups of six rats were given the same volume (0.2 ml: 100 g$^{-1}$) of carrier fluid at the same time prior to the challenge.

The results were calculated as follows: % inhibition of PCA = 100 (1−a/b) where a = the sum of the diameters of the wheals produced in the test animal at the sites of antibody dilutions as used in control groups and b = the mean sum of the diameters of the wheals produced in the control groups of animals at those antibody sites where at least five out of six of the animals gave less than maximum response. A typical variation in the control group of animals was SEM±6%.

| Compound of | Route | Carrier Fluid | Time* (mins) | Dose mg/kg | % inhibition of rat PCA |
|---|---|---|---|---|---|
| Example 1e | sc | PBS with NaHCO$_3$ | 10' | 5 | 42 |
|  |  |  | 30' | 5 | 18 |
|  |  |  | 10' | 20 | 57 |
|  |  |  | 30' | 20 | 41 |
| Example 1f | sc | PBS with NaHCO$_3$ | 10' | 10 | 32 |
|  |  |  | 30' | 10 | 19 |

*Time between administration of compound and antigen challenge.

Toxicity

No toxic effects were observed in any of the tests reported above.

We claim:

1. A compound of the formula (I):

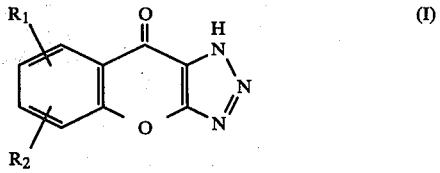

or a pharmaceutically acceptable salt thereof, wherein R$_1$ is hydrogen or alkyl of 1 to 6 carbon atoms, and R$_2$ is hydroxy, alkylsulphonyloxy of 1 to 4 carbon atoms in the alkyl moiety, or p-toluenesulphonyloxy.

2. A compound according to claim 1 of formula (II):

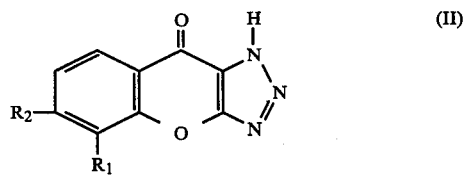

or a pharmaceutically acceptable salt thereof, wherein R$_1$ is hydrogen or alkyl of 1 to 6 carbon atoms and R$_2$ is hydroxy, alkylsulphonyloxy of 1 to 4 carbon atoms in the alkyl moiety, or p-toluenesulphonyloxy.

3. A compound according to claim 2, which is 6-mesyloxy-5-methyl-9-oxo-1H,9H-benzopyrano[2,3-d]-v-triazole, 6-hydroxy-5-methyl-9-oxo-1H,9H-benzopyrano[2,3-d]-v-triazole or 6-hydroxy-9-oxo-1H,9H-benzopyrano[2,3-d]-v-triazole, or a pharmaceutically acceptable salt thereof.

4. A compound according to claim 1 wherein R$_1$ is hydrogen, methyl, ethyl, n-propyl or isopropyl.

5. A compound according to claim 1 wherein R$_1$ is hydrogen, methyl or n-propyl.

6. A compound according to claim 1 wherein R$_2$ is hydroxy.

7. A compound according to claim 1 wherein R$_2$ is methanesulphonyloxy or p-toluenesulphonyloxy.

8. A compound according to claim 1 wherein R$_1$ when it is other than hydrogen is in the 5-position.

9. A compound according to claim 1 wherein R$_2$ is in the 6-position.

10. A compound according to claim 1 wherein R$_1$ is hydrogen, methyl or n-propyl and R$_2$ is hydroxy, methanesulphonyloxy or p-toluenesulphonyloxy.

11. A compound according to claim 1 in the form of a pharmaceutically acceptable salt, wherein the salt is an aluminum salt, an alkali metal salt or an alkaline earth metal salt.

12. A salt according to claim 11 which is the sodium, potassium, magnesium or ammonium salt.

13. The compound according to claim 1 which is 6-mesyloxy-5-methyl-9-oxo-1H,9H-benzopyrano[2,3-d]-v-triazole.

14. A pharmaceutical composition useful for the prophylaxis or treatment of diseases due to allergic response in mammals which comprises a therapeutically effective amount of a compound of the formula (I):

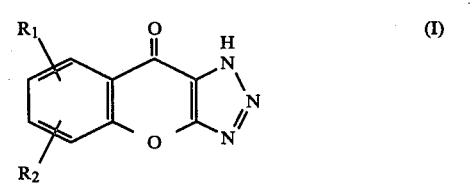

or a pharmaceutically acceptable salt thereof, wherein R$_1$ is hydrogen or alkyl of 1 to 6 carbon atoms, and R$_2$ is hydroxy, alkylsulphonyloxy of 1 to 4 carbon atoms in the alkyl moiety, or p-toluenesulphonyloxy, in combination with a pharmaceutically acceptable carrier.

15. A composition according to claim 14 wherein the compound is of the formula (II):

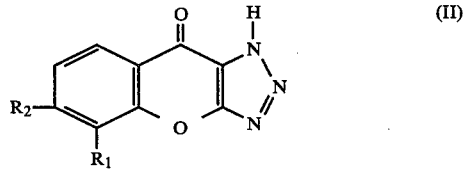

or a pharmaceutically acceptable salt thereof, wherein R$_1$ is hydrogen or alkyl of 1 to 6 carbon atoms and R$_2$ is hydroxy, alkylsulphonyloxy of 1 to 4 carbon atoms in the alkyl moiety, or p-toluenesulphonyloxy, in combination with a pharmaceutically acceptable carrier.

16. A composition of according to claim 14 wherein R$_1$ is hydrogen, methyl, ethyl, n-propyl or isopropyl.

17. A composition according to claim 14 wherein R$_1$ is hydrogen, methyl or n-propyl.

18. A composition according to claim 14 wherein R$_2$ is hydroxy.

19. A composition according to claim 14 wherein R$_2$ is methanesulphonyloxy or p-toluenesulphonyloxy.

20. A composition according to claim 14 wherein R₁ when it is other than hydrogen is in the 5-position.

21. A composition according to claim 14 wherein R₂ is in the 6-position.

22. A composition according to claim 14 wherein R₁ is hydrogen, methyl or n-propyl and R₂ is hydroxy, methanesulphonyloxy or p-toluenesulphonyloxy.

23. A composition according to claim 14 wherein the compound is in the form of a pharmaceutically acceptable salt, wherein the salt is an aluminum salt, an alkali metal salt or an alkaline earth metal salt.

24. A composition according to claim 14 wherein the compound is in the form of the sodium, potassium, magnesium or ammonium salt.

25. A composition according to claim 14 wherein the compound is 6-mesyloxy-5-methyl-9-oxo-1H,9H-benzopyrano[2,3-d]-v-triazole.

26. A composition according to claim 14 in oral administration form.

27. A composition according to claim 14 in parenteral administration form.

28. A composition according to claim 14 in topical application form.

29. A composition according to claim 14 in rectal administration form.

30. A method for the prophylaxis or treatment of diseases due to an allergic response in mammals which comprises administering to a mammal in need thereof a therapeutically effective amount of a compound of the formula (1):

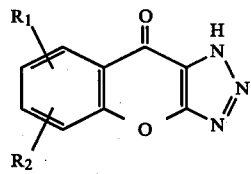

(I)

or a pharmaceutically acceptable salt thereof, wherein R₁ is hydrogen or alkyl of 1 to 6 carbon atoms, and R₂ is hydroxy, alkylsulphonyloxy of 1 to 4 carbon atoms in the alkyl moiety, or p-toluenesulphonyloxy, in combination with a pharmaceutically acceptable carrier.

31. A method according to claim 30 wherein the compound is of the formula (II):

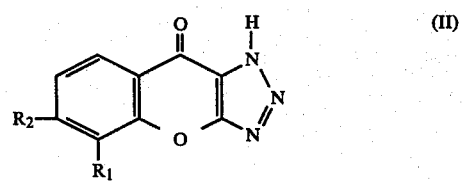

(II)

or a pharmaceutically acceptable salt thereof, wherein R₁ is hydrogen or alkyl of 1 to 6 carbon atoms and R₂ is hydroxy, alkylsulphonyloxy of 1 to 4 carbon atoms in the alkyl moiety, or p-toluenesulphonyloxy, in combination with a pharmaceutically acceptable carrier.

32. A method according to claim 30 wherein R₁ is hydrogen, methyl, ethyl, n-propyl or isopropyl.

33. A method according to claim 30 wherein R₁ is hydrogen, methyl ot n-propyl.

34. A method according to claim 30 wherein R₂ is hydroxy.

35. A method according to claim 30 wherein R₂ is methanesulphonyloxy or p-toluenesulphonyloxy.

36. A method according to claim 30 wherein R₁ when it is other than hydrogen is in the 5-position.

37. A method according to claim 30 wherein R₂ is in the 6-position.

38. A method according to claim 30 wherein R₁ is hydrogen, methyl or n-propyl and R₂ is hydroxy, methanesulphonyloxy or p-toluenesulphonyloxy.

39. A method according to claim 30 wherein the compound is in the form of a pharmaceutically acceptable salt, wherein the salt is in aluminum salt, an alkali metal salt or an alkaline earth metal salt.

40. A method according to claim 30 wherein the compound is in the form of the sodium, potassium, magnesium or ammonium salt.

41. A method according to claim 30 wherein the compound is 6-mesyloxy-5-methyl-9-oxo-1H,9H-benzopyrano[2,3-d]-v-triazole.

42. A method according to claim 30 wherein the administration is oral.

43. A method according to claim 30 wherein the administration is parenteral.

44. A method according to claim 30 wherein the administration is by topical application.

45. A method according to claim 30 wherein the administration is rectal.

* * * * *